United States Patent
Meinel et al.

(10) Patent No.: US 11,891,352 B2
(45) Date of Patent: Feb. 6, 2024

(54) AMINOMETHYL-FUNCTIONALIZED DENATONIUM DERIVATIVES, THEIR PREPARATION AND USE

(71) Applicant: Julius-Maximilians-Universitaet Wuerzburg, Wuerzburg (DE)

(72) Inventors: Lorenz Meinel, Wuerzburg (DE); Tessa Luehmann, Wuerzburg (DE); Martina Raschig, Wuerzburg (DE)

(73) Assignee: Julius-Maximilians-Universitaet, Wuerzburg (DE)

( * ) Notice: Subject to any disclaimer, the term of this patent is extended or adjusted under 35 U.S.C. 154(b) by 839 days.

(21) Appl. No.: 16/975,077

(22) PCT Filed: Feb. 20, 2019

(86) PCT No.: PCT/EP2019/054140
§ 371 (c)(1),
(2) Date: Aug. 21, 2020

(87) PCT Pub. No.: WO2019/162289
PCT Pub. Date: Aug. 29, 2019

(65) Prior Publication Data
US 2021/0087138 A1 Mar. 25, 2021

(30) Foreign Application Priority Data
Feb. 21, 2018 (EP) .................................. 18157816

(51) Int. Cl.
C07C 237/04 (2006.01)
C07C 231/12 (2006.01)
C07K 1/10 (2006.01)

(52) U.S. Cl.
CPC .......... *C07C 237/04* (2013.01); *C07C 231/12* (2013.01); *C07K 1/10* (2013.01)

(58) Field of Classification Search
CPC ........ C07C 237/04; C07C 231/12; C07K 1/10
See application file for complete search history.

(56) References Cited

U.S. PATENT DOCUMENTS

2019/0185416 A1* 6/2019 Wyrwa ................. C07C 269/04

OTHER PUBLICATIONS

Saroli, Alfred, "Struktur-Aktivitätsbeziehung von Bitterverbindungen im Hinblick zu Denatoniumchlorid und Dipeptidmethylesters", *Zeitschrift Fuer Lebensmitteluntersuchung Und Forschung*, vol. 182, No. 2, pp. 118-120 (Feb. 1, 1986).

* cited by examiner

*Primary Examiner* — Li N Komatsu
(74) *Attorney, Agent, or Firm* — Smith Patent, LLC; Chalin A. Smith

(57) ABSTRACT

The present invention is directed to compounds of the general formula (I) and salts thereof

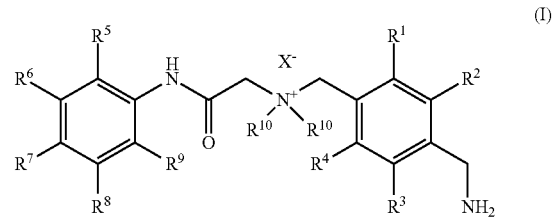

wherein $X^-$ is halide, pseudohalide, sulphate, benzoate, acetate, trifluoroacetate, hydroxide, saccharinate or capsaicinate; $R^{10}$ is hydrogen or C1-C10-alkyl; and $R^1$-$R^9$ independently are hydrogen, halogen, C1-C5-alkyl, C1-C4-alkoxy, C1-C20-alkoxycarbonyl. The invention is furthermore directed to a method for the preparation of these compounds. The compounds can be used as bitter substances in medicine, pharmaceutics and/or diagnostics. They can furthermore be used for the coupling to proteins and peptides by means of forming a peptide bond between the amino-group of the compounds of the present invention and a carboxyl-group of the protein or peptide.

18 Claims, 6 Drawing Sheets

Specification includes a Sequence Listing.

SEQUENCE LISTING

```
<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: synthetic construct

<400> SEQUENCE: 1

Gln Pro Val Val
1

<210> SEQ ID NO 2
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: triphenylmethyl (Trt) protecting group

<400> SEQUENCE: 2

Gln Pro Val Val
1

<210> SEQ ID NO 3
<211> LENGTH: 4
<212> TYPE: PRT
<213> ORGANISM: Artificial Sequence
<220> FEATURE:
<223> OTHER INFORMATION: synthetic construct

<400> SEQUENCE: 3

Asp Ala Pro Val
1

<210> SEQ ID NO 4
<211> LENGTH: 4
<212> TYPE: PRT
```

```
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: tert-butyl (tBu) protecting group

<400> SEQUENCE: 4

Asp Ala Pro Val
1

<210> SEQ ID NO 5
<211> LENGTH: 8
<212> TYPE: PRT
<213> ORGANISM: Artificial Sequence
<220> FEATURE:
<223> OTHER INFORMATION: synthetic construct

<400> SEQUENCE: 5

Gly Pro Gln Gly Ile Ala Gly Ala
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: triphenylmethyl (Trt) protecting group

<400> SEQUENCE: 6

Gly Pro Gln Gly Ile Ala Gly Ala
1               5
```

AMINOMETHYL-FUNCTIONALIZED DENATONIUM DERIVATIVES, THEIR PREPARATION AND USE

PRIORITY

This application corresponds to the U.S. National phase of International Application No. PCT/EP2019/054140, filed Feb. 20, 2019, which, in turn, claims priority to European Patent Application No. 18157816.2 filed Feb. 21, 2018, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Aug. 4, 2023, is named LNK219US_SLST25.txt and is 1,645 bytes in size.

TECHNICAL FIELD OF THE PRESENT INVENTION

The present invention is directed to aminomethyl ($NH_2$—$CH_2$—)-functionalized derivatives of the known quaternary ammonium compound denatonium, as well as to a method for the synthesis of these compounds. The compounds of the present invention are stable and provide a bitter taste despite the functionalization. The amino-group of these compounds is useful for the coupling of the compounds with peptides and proteins. This has application potential in the field of medicine, biology, pharmaceutics and cosmetics.

BACKGROUND OF THE PRESENT INVENTION

Apart from naturally occurring bitter substances such as quinine and caffeine, a number of synthetic bitter substances are known. One class of these bitter substances are quaternary ammonium compounds [A. Saroli, Z. Lebensm. Unters. Forsch. 182, 1986, 118-120]. These include, among others, the substance benzyldiethyl(2,6-xylyl-carbamoyl)methylammonium benzoate, also designated as denatonium benzoate, a product marketed by Veranova under the tradename Bitrex®, which has the following structure:

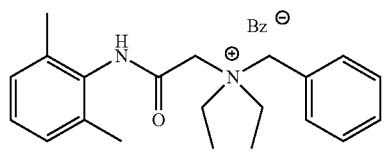

Further salts of denatonium are denatonium saccharide [U.S. Pat. No. 4,652,577 A] and capsaicinate [DE 698 24 191 T2].

Due to its bitter taste, denatonium benzoate is used as an additive in common household products in order to avoid unintentional swallowing. Moreover, it is useful for denaturing ethanol and other alcohols, which are used as solvents and cleaning agents. Furthermore, it is useful as an additive in nail varnish against nail biting.

By introducing one or more functional groups into denatonium or derivatives thereof, the application spectrum of these compounds as bitter substance could be further expanded because the functional group would allow for the coupling of these compounds to other molecules.

From US 2009/0306429 A1, denatonium derivatives are known, which are chloro-substituted in ortho- or para-position of the benzyl group. However, it is not disclosed in US 2009/0306429 A1 if and how these denatonium compounds can be further functionalized.

In a recently filed German patent application (application number: DE 10 2016 009 766.3), denatonium derivatives are disclosed which can be coupled to a metal, ceramic, glass or polymeric surface via a peptide residue or a hydrocarbon residue, optionally via an additional linker group being a peptide, polyester, polyamide, hydrocarbon or polyethylenglycol linker group.

In particular, it would be desirable to have a functionalization in denatonium or denatonium derivatives that allows for the coupling of these compounds to peptides and proteins since this would further expand the application spectrum of these bitter substances. In this regard, an amino-functionality (i.e. an $NH_2$ group) would be beneficial because in that case, a peptide coupling with a peptide or protein, in particular with a terminal carboxyl-group of the peptide or protein, could be achieved. Neither in US 2009/0306429 A1 nor in DE 10 2016 009 766.3, amino-functionalized denatonium derivatives are disclosed.

There is, however, the difficulty to provide amino-functionalized denatonium derivatives, which are stable and which maintain their bitter taste. In their effort to solve this problem, the inventors prepared the denatonium derivative (1), which comprises an aromatic $NH_2$-group:

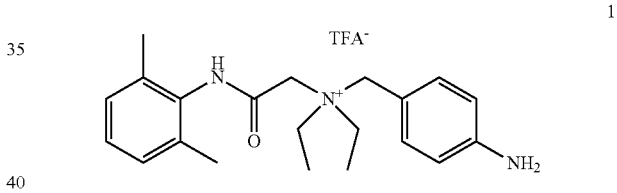

By way of LC/MS measurements, however, it was found that this derivative is not stable and thus not suitable for the coupling with peptides and proteins. The decomposition of the substance is illustrated as follows:

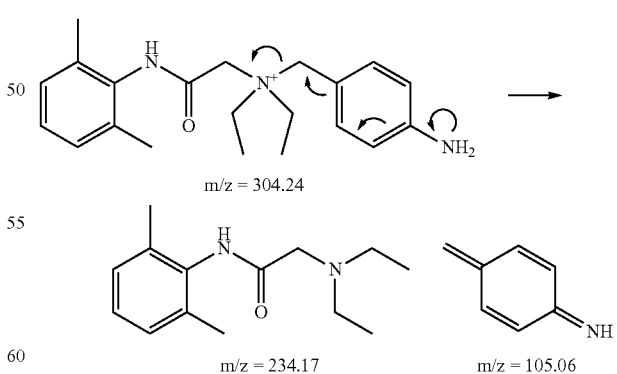

Since derivative (1) was found to be instable and, in consequence, not suitable for the coupling with peptides and proteins, there is an urgent need for the provision of other amino-functionalized denatonium derivatives in order to expand the already various fields of application. The problem underlying the present invention is thus the provision of stable amino-functionalized denatonium derivatives, which, despite the functionalization, maintain the bitter taste of the denatonium, as well as a method for their preparation.

SUMMARY OF THE PRESENT INVENTION

This problem is solved according to present invention by a compound of general formula (I) or a salt thereof

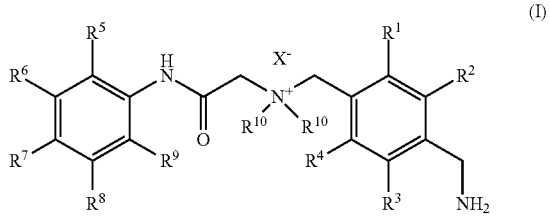

(I)

wherein
X⁻ is halide, pseudohalide, sulphate, benzoate, acetate, trifluoroacetate, hydroxide, saccharinate or capsaicinate,
$R^{10}$ is hydrogen or C1-C10-alkyl,
$R^1$-$R^9$ independently are hydrogen, halogen, C1-C5-alkyl, C1-C4-alkoxy, C1-C20 alkoxycarbonyl.

In the context of the present invention, a salt of the compound of formula (I) refers to an ammonium salt of the compound of formula (I), which has a structure according to the following formula (Ia):

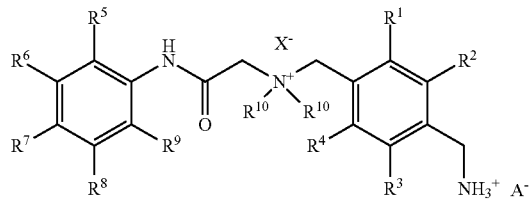

(Ia)

A⁻ in the compound of formula (Ia) can be halide, pseudohalide, sulphate, benzoate, acetate, trifluoroacetate, hydroxide, saccharinate or capsaicinate, and is preferably identical with X⁻. Accordingly, the preferred embodiments for X⁻ which will be described herein below correspond to the preferred embodiments for K.

"Alkyl", as used herein, means linear and, if applicable in view of the number of carbon atoms in the alkyl group, also branched hydrocarbon residues of the general formula $C_nH_{2n+1}$, wherein n indicates the number of carbon atoms of the alkyl residue. Thus, C3-alkyl comprises for example n-propyl and iso-propyl. C4-alkyl comprises n-butyl, iso-butyl and tert-butyl. Corresponding constitutional isomers exist also for C5-C10-alkyl, C3-C4-alkoxy and C3-C20-alkoxycarbonyl.

In compounds of general formula (I) or the salts thereof, "halide" means in particular chloride (Cl⁻), bromide (Br⁻) and iodide (I⁻).

In compounds of general formula (I) or the salts thereof, "pseudohalide" means in particular tosylate (p-Me-$C_6H_4$—$SO_3^-$) and mesylate ($MeSO_3^-$).

In compounds of general formula (I) or the salts thereof, "halogen" means in particular fluoro (F), chloro (Cl), bromo (Br) and iodo (I).

Preferred in the present invention are compounds of formula (I) or the salts thereof, wherein
X⁻ is halide, pseudohalide, sulphate, benzoate, acetate or trifluoroacetate,
$R^{10}$ is C1-C4-alkyl,
$R^1$-$R^4$ is hydrogen,
$R^5$ is C1-C4-alkyl,
$R^6$-$R^8$ is hydrogen,
$R^9$ is C1-C4-alkyl.

Particularly preferred in the present invention is a compound of formula (I) or a salt thereof, wherein
X⁻ is trifluoroacetate,
$R^{10}$ is ethyl,
$R^5$ is methyl,
$R^9$ is methyl,
$R^1$-$R^4$ is hydrogen,
$R^6$-$R^8$ is hydrogen.

A particularly preferred compound of general formula (I) represents a trifluoroacetic acid (TFA) salt, which is disclosed herein as "compound 2" and has the following structure (TFA⁻ means $F_3CCO_2^-$):

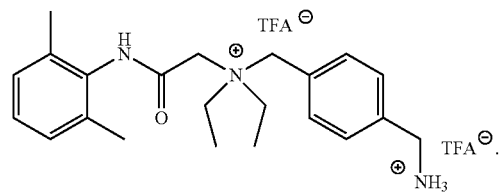

2

The preferred embodiments of the compound of general formula (I) or a salt thereof according to the present invention are also specified in sub-claims 2 and 3.

DETAILED DESCRIPTION OF THE PREFERRED EMBODIMENTS

Figure 1:
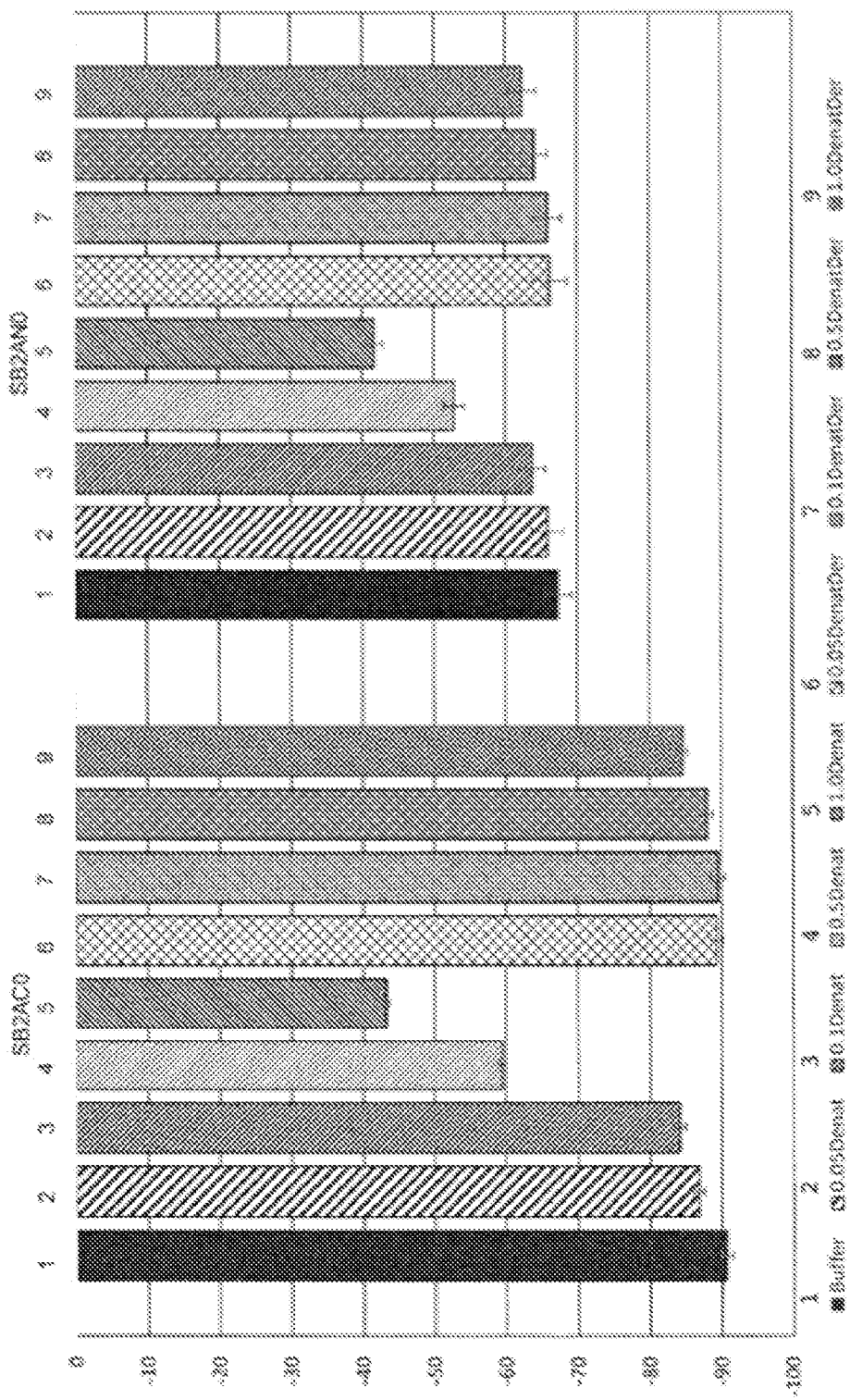
FIG. 1 is a graphical illustration of the potentials measured for compound 2 ("DenatDer") of the invention and denatonium benzoate ("Denat") at different concentrations, using an electronic tongue, in particular the sensors SB2AC0 and SB2AN0.

It has surprisingly been found that compounds of general formula (I) or salts thereof are stable, i.e. can be used for further functionalizing via the free amino group, in particular in the coupling with proteins and peptides having a terminal carboxyl group (COOH-group). Despite the functionalization with an amino-methyl-group, the compounds of the present invention provide a bitter taste.

Determining the bitter taste of the compounds of the present invention can for example be achieved using an "electronic tongue", which includes determining the electronic potentials of the substance in aqueous solution in a defined concentration. This method is known to the skilled person, and is also illustrated in the examples provided herein. For carrying out the measurement of the electronic potentials using the electronic tongue, it is necessary to protect the free amino group of the compounds disclosed herein, e.g. by means of acetylation. The acetylation of the free amino group is thus part of the analytics and can be achieved by routine reactions known to the skilled person. The results measured with the acetylated compounds are indicative for the bitter taste of the unprotected compounds disclosed herein.

The above problem is furthermore solved by a method for the preparation of a compound of general formula (I) comprising the following steps (as also defined in claim 4):

a) reacting a compound of general formula (II)

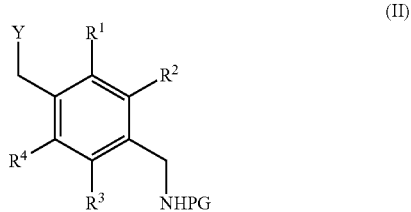

with a compound of general formula (III)

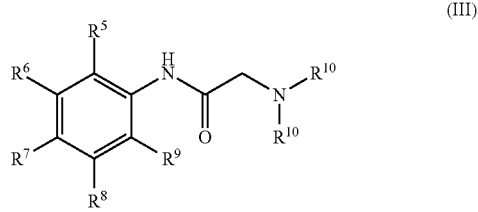

resulting in the formation of a compound of general formula (IV)

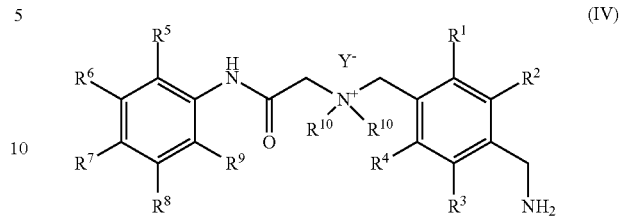

b) deprotecting the compound of general formula (IV) resulting in the formation of the compound of general formula (I) or a salt thereof, wherein in the compounds of general formulae (I), (II), (III) and (IV)

$R^{10}$ is hydrogen or C1-C10-alkyl, $R^1$-$R^9$ independently are hydrogen, halogen, C1-C5-alkyl, C1-C4-alkoxy, C1-C20-alkoxycarbonyl, Y is halogen or pseudohalogen, $Y^-$ is the halide or pseudohalide corresponding to Y, and PG is an amino protection group, selected from the group Boc, Cbz, Fmoc and alloc.

The method according to the invention for the preparation of the compounds according to the invention is efficient since reaction times are short and the yields are good. Preferred embodiments of the method according to the invention are also defined in sub-claims 5 to 10 and will be further described in the following.

In the compound of general formulae (II), "halogen" is in particular chloro (Cl), bromo (Br) or iodo (I). "Pseudohalogen" in the compound of general formulae (II) is in particular p-Me-$C_6H_4$—$SO_3$— or $MeSO_3$—. Preferably, the bromo-substituted compound of general formula (II) is used in the method according to the present invention (wherein thus Y=Br).

In the compound of general formulae (IV), "halide" is in particular chloride ($Cl^-$), bromide ($Br^-$) or iodide ($I^-$). "Pseudohalide" in the compound of general formulae (IV) is in particular tosylate (p-Me-$C_6H_4$—$SO_3^-$) or mesylate ($MeSO_3^-$). Preferably $Y^-$=$Br^-$ in the compound of general formula (IV) in the method according to the present invention.

The meaning of the abbreviations "Boc" (tert-butyloxycarbonyl), "Cbz" (benzyloxycarbonyl), "Fmoc" (fluorenylmethoxycarbonyl) and "alloc" (allyloxycarbonyl) is known to the skilled person because it is part of his technical knowledge (see, e.g., Fernando Albericio et al., Chem. Rev. 2009, 109, 6, 2455-2504), and therefore it does not have to be further explained herein. In the method according to the present invention, the Boc-protected compound of formula (II) is preferably used (wherein thus PG=Boc).

Preferably, $R^1$ to $R^{10}$ in the compounds of general formulae (I), (II), (III) and (IV) in the method according to the present invention are defined as follows:

$R^{10}$ is C1-C4-alkyl, $R^1$-$R^4$ is hydrogen, $R^5$ is C1-C4-alkyl, $R^6$-$R^8$ is hydrogen, $R^9$ is C1-C4-alkyl.

Particularly preferred, $R^1$ to $R^{10}$ in the compounds of general formulae (I), (II), (III) and (IV) in the method according to the present invention are defined as follows:

$R^{10}$ is ethyl,
$R^5$ is methyl,
$R^9$ is methyl,
$R^1$-$R^4$ is hydrogen,
$R^6$-$R^8$ is hydrogen.

The compounds of general formulae (II) and (III) are either commercially available or can be prepared by the skilled person by using his common general knowledge.

In the method according to the invention, the compounds of general formulae (II) and (III) react in step a) in a nucleophilic substitution to give the compound of general formula (IV). This reaction can be performed by using a solvent, wherein the skilled person selects a suitable solvent from the range of common solvents known to him, comprising for example, but not limited thereto, dichloromethane, ethyl acetate, tetrahydrofurane, toluene and di methylformamide.

The reaction according to step a) of the method according to the invention is however preferably performed without using a solvent, i.e. solvent-free. In this case, the starting compounds are mixed and heated to a melt, which typically requires heating of the mixture of starting compounds to temperatures of from 60 to 120° C., preferably from 70 to 110° C., particularly preferred from 80 to 100° C. The reaction in the melt has the advantage that the reaction times are short, which means that they are in the range of from 1 to 30 min, preferably from 2 to 20 min, particularly preferred from 5 to 15 min. Carrying out step a) solvent-free contributes to the environmental friendliness and cost-efficiency of the method of the present invention.

Typically, the reaction according to step a) of the method according to the invention is performed with 1 molar equivalent of the compound of general formula (II) and 1.4-1.8 molar equivalents, preferably 1.5-1.7 molar equivalents of the compound of general formula (III).

Upon coupling the compounds of formulae (II) and (III) in step a), the reaction mixture comprising the reaction product of general formula (IV) is typically added to a solvent or a solvent mixture, which leads to the precipitation of the product, which can then be filtered off. The reaction product of general formula (IV) should thus be poorly soluble in the solvent or solvent mixture of choice. The skilled person will select a suitable solvent or a solvent mixture for precipitating the compound of general formula (IV) from the spectrum of the common solvents known to him, comprising for example, but not limited to ethyl acetate, hexane, diethylether, dichloromethane, acetone, tetrahydrofuran and toluene.

The precipitated reaction product of step a), i.e. the compound of general formula (IV), is subsequently deprotected in step b) of the method according to the present invention, which means that the amino protection group is cleaved in order to provide the compound of formula (I), i.e. the compound of the present invention. The deprotection of Boc-, Cbz-, Fmoc- and alloc-protected amino groups can be achieved by applying routine methods known to the skilled person.

Depending on the amino protecting group used in the compound of formula (IV) and the method applied to cleave it, the compound of formula (I) or a salt thereof according to formula (Ia) results from the cleaving step b).

If, for example, a Boc group is used as the amino protecting group in the compound of formula (IV), and the Boc group is cleaved with an acid, such as trifluoroacetic acid, hydrobromic acid, hydrochloric acid, p-toluenesulfonic acid, methanesulfonic acid, acetic acid or benzoic acid, a salt of the compound of formula (I) according to formula (Ia) results from the deprotection step b), wherein $A^- = X^-$.

Preferably, a Boc-group is used as the amino protecting group in the method according to the present invention. This has the advantage that the deprotection can be carried out solvent-free, preferably by reacting the compound of general formula (IV) at room temperature in trifluoroacetic acid without using additional solvent. Following this procedure, a salt of the formula (I) according to formula (Ia) results, wherein $A^- = X^- = TFA^-$.

The reaction product of the deprotection step b), i.e. the compound of general formula (I), is then typically precipitated from a suitable solvent or solvent mixture, which the skilled person selects from the range of common solvents known to him, comprising, but not limited to ethyl acetate, hexane, diethylether, dichloromethane, acetone, tetrahydrofuran and toluene.

In an embodiment of the method according to the present invention, compound 2

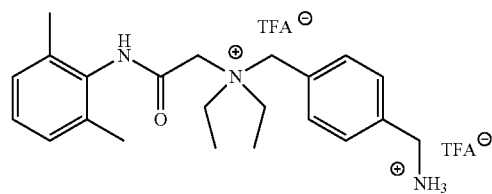

is prepared in a nucleophilic substitution with subsequent deprotection from the commercially available starting compounds tert-butyl-4-(bromomethyl)benzylcarbamate and lidocaine (2-diethylamino-N-(2,6-dimethylphenyl)acetamide) and as illustrated below:

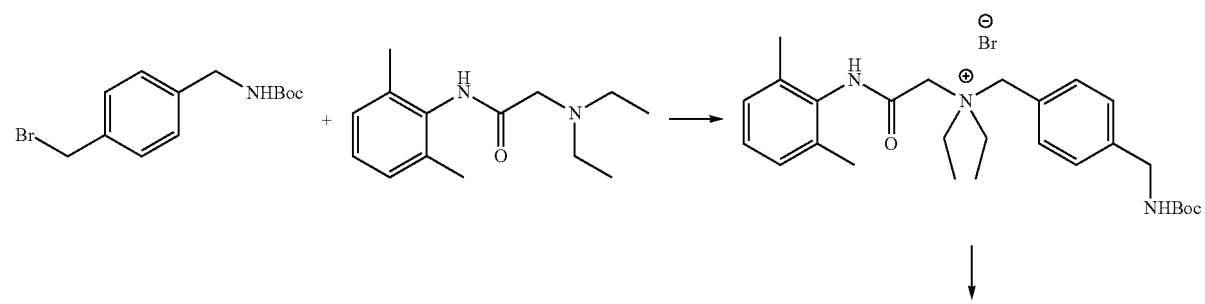

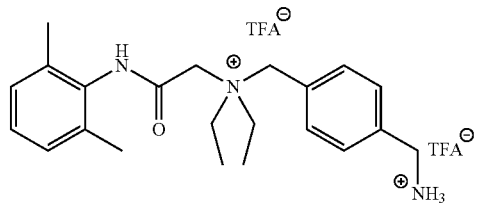

In the first step, 1 equivalent of tert-butyl-4-(bromomethyl)benzylcarbamate and 1.5-1.6 equivalents of lidocaine are heated under stirring at 80° C. until they are melted. After a few minutes the molten mixture becomes highly viscous, up to solid. After a resting period of 10 minutes, at 80° C., a mixture consisting of ethyl acetate and n-hexane (1:1) was added to the obtained yellow solid. This solid is stirred for 10 minutes at 80° C. in the mixture and the white residue resulting therefrom is filtered off. For the deprotection, the white solid is treated with trifluoroacetic acid and stirred for 1 hour. The raw product is subsequently precipitated from diethylether and filtered off.

As already stated above, the compounds of general formula (I) or salts thereof provide a bitter taste despite the functionalization with an aminomethyl-group. Therefore, the compounds of general formula (I) or salts thereof according to the present invention are suitable for use as bitter substances.

Due to the aminomethyl-functionalization, the compounds of general formula (I) or salts thereof are particularly suitable for the coupling to peptides and proteins applying peptide-coupling chemistry.

The present invention thus also provides a coupling product of a compound according to formula (I) as defined in claims 1 to 3 and a peptide or a protein, wherein the compound of general formula (I) and the peptide or the protein are connected via a peptide bond between the aminomethyl-group of the compound of formula (I) and the carboxyl-group (COOH-group) of the peptide or protein.

Peptides, as used herein, refers a chain of amino acids comprising less than 50 amino acids. The chain can be branched or unbranched.

A "protein", as used herein, refers to a biomolecules comprising at least one polypeptide chain, which contains at least 50 amino acids. The at least one polypeptide chain can be branched or unbranched.

The peptides and proteins for use herein have a terminal carboxyl-group. The peptide or protein can also be bound to other molecules, such as sugars (e.g. oligosaccharides, polysaccharides), polymers, nucleic acids (e.g. DNA and RNA), ligands, coenzymes and cofactors.

If the coupling product of the present invention is reacted with an aminopeptidase, the peptide bonds in the peptide or protein moiety of the coupling product are hydrolyzed and the peptide or protein degrades. This leads to the release of the compound of the present invention, which can then be perceived by a human patient in terms of its bitter taste. This reaction can be used for diagnostic purposes. Accordingly the coupling product of the present invention can be used in medicine, pharmaceutics and/or diagnostics.

The present invention also provides a method for producing the coupling product of the invention, said method comprising coupling a compound of general formula (I) or a salt thereof with a peptide or protein by forming a peptide bond between the aminomethyl-group of the compound of general formula (I) or the salt thereof and a carboxyl-group of the protein or peptide. "Forming a peptide bond" between a carboxyl-group of the protein or peptide and the aminomethyl-group of the compound of general formula (I) thus means that the protein or peptide and the compound of general formula (I) of the invention are coupled.

Depending on its structure, the peptide or protein can optionally be used in protected form in the coupling with the compound of general formula (I) or the salt thereof, i.e. has to be protected by a protection group. The skilled person will choose the protection group according to his needs on the basis of his common general knowledge. The protection group can then be cleaved from the coupling product after the coupling. Such a procedure is illustrated in Examples 4 and 5 provided herein.

The method for producing the coupling product is preferably carried out in the presence of a coupling agent, preferably HATU, and a base, preferably DIPEA.

In a particularly preferred embodiment of the method for producing the coupling product, a peptide or protein is shaken under light exclusion with the coupling agent HATU ([O-(7-azabenzotriazol-1-yl)-N,N,N',N'-tetramethyluronium-hexafluorphosphate]), DIPEA (diisopropylethylamine) and a compound of general formula (I) or a salt thereof in dry DMF overnight. This procedure is illustrated in Examples 4 and 5 provided herein.

The procedure disclosed herein is for example useful for the coupling of compounds of the present invention with a peptide-based active agent, i.e. to a compound with pharmaceutical activity, said active agent being a peptide itself or at least comprising a peptide residue with a terminal carboxyl-group.

Thus, the present invention also relates to compounds of general formula (I) as disclosed herein for use as a bitter substance in medicine, pharmaceutics and/or diagnostics, in particular if they are coupled to compounds with pharmaceutical activity, such as peptide-based active agents, providing the coupling products of the present invention. After cleavage of the coupling product, the compound of the present invention will be released and the bitter taste will be perceived by a human patient.

In sum, the present invention is directed to:
(i). Compound of general formula (I) (as shown above) or a salt thereof, wherein
 X$^-$ is halide, pseudohalide, sulphate, benzoate, acetate, trifluoroacetate, hydroxide, saccharinate or capsaicinate,
 R$^{10}$ is hydrogen or C1-C10-alkyl,
 R$^1$-R$^9$ independently are hydrogen, halogen, C1-C5-alkyl, C1-C4-alkoxy, C1-C20-alkoxycarbonyl.
(ii). Compound according to item (i), wherein in general formula (I)
 X$^-$ is halide, pseudohalide, sulphate, benzoate, acetate or trifluoroacetate,
 R$^{10}$ is C1-C4-alkyl, $R^1$-$R^4$ is hydrogen,
$R^5$ is C1-C4-alkyl,
$R^9$ is C1-C4-alkyl,
$R^6$-$R^8$ is hydrogen.
(iii). Compound according to item (i) or (ii), wherein in general formula (I)
X⁻ is trifluoroacetate,
$R^{10}$ is ethyl,
$R^5$ is methyl,
$R^9$ is methyl,
$R^1$-$R^4$ is hydrogen,
$R^6$-$R^8$ is hydrogen.
(iv). Method for the preparation of a compound of general formula (I) (as shown above) or a salt thereof, comprising the following steps:
  a) reacting a compound of general formula (II) (as shown above) with a compound of general formula (III) (as shown above) resulting in the formation of a compound of general formula (IV) (as shown above),
  b) deprotecting the compound of general formula (IV) resulting in the formation of the compound of general formula (I) or a salt thereof,
  wherein in the compounds of general formulae (I), (II), (III) and (IV)
  $R^1$-$R^{10}$ are defined as in item (i), preferably as in item (iii), and particularly preferably as in item (iii),
  Y is halogen or pseudohalogen,
  Y⁻ is the halide or pseudohalide corresponding to Y, and
  PG is an amino protection group, selected from the group Boc, Cbz, Fmoc and alloc.
(v). Method according to item (iv), wherein step a) is performed in a solvent-free melt.
(vi). Method according to item (v), wherein a mixture of the compound of general formula (II) and the compound of general formula (III) is heated for 1 to 30 min at temperatures in the range of 60 to 120° C.
(vii). Method according to any of items (iv) to (vi), wherein 1 equivalent of the compound of general formula (II) is reacted with 1.4 to 1.8 equivalents of the compound of general formula (III).
(viii). Method according to any of items (iv) to (vii), wherein in the compound of general formula (II) Y is Br and in the compound of general formula (IV) Y⁻ is Br⁻.
(ix). Method according to any one of items (iv) to (viii), wherein PG in the compound of general formulae (II) and (IV) is Boc.
(x). Method according to item (ix), wherein the deprotection of the compound of general formula (IV) in step b) is performed solvent-free using trifluoroacetic acid.
(xi). Use of a compound according to items (i) to (iii) as a bitter substance.
(xii). Coupling product of a compound according to formula (I) as defined in items (i) to (iii) and a peptide or a protein, wherein the compound of general formula (I) and the peptide or the protein are connected via a peptide bond between the aminomethyl-group of the compound of formula (I) and the carboxyl-group (COOH-group) of the peptide or protein.
(xiii). Method for producing a coupling product as defined in item (xii), comprising coupling a compound of general formula (I) or a salt thereof with a peptide or protein by forming a peptide bond between the aminomethyl-group of the compound of general formula (I) or the salt thereof and a carboxyl-group of the protein or peptide.
(xiv). Method according to item (xiii), wherein the peptide or protein used in the coupling with the compound of general formula (I) or the salt thereof is protected by a protection group, and the protection group is cleaved after the coupling.
(xv). Method according to item (xiii) or (xiv), wherein the compound of general formula (I) or the salt thereof and the peptide or protein is coupled in the presence of a coupling agent, preferably HATU, and a base, preferably DIPEA.

The following examples shall illustrate the invention without limiting the scope of the claimed subject matter.

EXAMPLES

Example 1: Synthesis of Denatonium-$CH_2$-NHBoc 1.2 g lidocain (5.2 mmol) and 1.0 g tert-butyl-4-(bromomethyl)benzylcarbamate (3.4 mmol) were heated to 80° C. until the formation of a yellow melt. The melt then became highly viscous, up to solid, and subsequently, after a resting period of 10 minutes at 80° C., the obtained yellow solid was treated with 40 mL of a mixture of ethyl acetate and n-hexane (1:1). To obtain the protected product, the yellow solid was stirred for 10 minutes at 80° C. in the mixture. The resulting white residue was filtered off and washed with a mixture of ethyl acetate and hexane (1:1). 1.6 g of the protected product were obtained.
Sum formula: $C_{27}H_{40}N_3O_3^+Br^-$
Molecular mass: 534.5 g/mol
Yield 1.6 g (91%).

Example 2: Synthesis of a Denatonium-$CH_2$—$NH_2$ Salt (Compound 2)

For the subsequent deprotection, 228 mg of the product (0.4 mmol) obtained from Example 1 was dissolved in 1 mL of trifluoroacetic acid and shaken at room temperature for 1 hour. The raw product was precipitated in diethylether and filtered off. The product was purified by chromatography.
Sum formula: $C_{22}H_{33}N_3O^{2+} 2\ C_2F_3O_2^-$
Molecular mass: 581.6 g/mol
Yield: 175 mg (75%).
¹H-NMR (DMSO, δ [ppm], J [Hz]): δ 10.14 (s, 1H), 8.30 (s, 3H), 7.62 (m, 4H), 7.20-7.10 (m, 3H), 4.84 (s. 2H), 4.18 (s, 2H), 4.12 (q. $^3J_{H,H}$=5.8, 2H), 3.54-3.48 (m, 4H), 2.20 (s, 6H), 1.42 (t, $^3J_{H,H}$=7.1, 6H).
¹³C-NMR (DMSO, δ [ppm], J [Hz]): δ 162.7 (s, 10), 136.8 (s, 10), 135.5 (s, 2C), 133.7 (s, 1C), 133.6 (s. 2C), 129.9 (s, 2C), 128.5 (s, 2C), 128.2 (s, 10), 127.7 (s, 10), 61.6 (s, 10), 56.0 (s, 10), 54.9 (s, 2C), 42.2 (s, 10), 18.6 (s, 2C), 8.3 (s, 2C).

Example 3: Taste Testing of a Denatonium-$CH_2$—$NH_2$Salt (Compound 2)

The potentials of the denatonium derivative prepared according to Examples 1 and 2 (i.e. compound 2, which, for the purpose of this measurement, has been acetylated on the free amino group) and, for comparison, of denatonium benzoate (given in brackets), measured by an electronic tongue are in the range of:
SB2AC0: 0.05 mM=−89 mV (−88 mV); 0.1 mM=−89 mV (−85 mV); 0.5 mM=−88 mV (−59 mV); 1.0 mM=−85 mV (−44 mV).
SB2AN0: 0.05 mM=−66 mV (−66 mV); 0.1 mM=−65 mV (−64 mV); 0.5 mM=−64 mV (−53 mV); 1 mM=−62 mV (−42 mV).
A graphic illustration of these results is provided in FIG. 1, wherein (acetylated) compound 2 of the invention is abbreviated as "DenatDer" and denatonium benzoate abbreviated as "Denat".

The sensors SB2AC0 and SB2AN0 measure bitter cationic substances. Denatonium benzoate is known to the skilled person, and it represents the corresponding non-substituted compound (which does not have an aminomethyl-functionalization, contrary to compound 2 according to the present invention).

Based on the data of the present example, it can be concluded that compounds according to the present invention are perceived similarly as denatonium benzoate by the electronic tongue. This allows the conclusion that compounds according to the invention are also perceived as bitter in taste by humans.

In a further measurement of (acetylated) compound 2 of the invention in comparison with denatonium benzoate in a concentration range of 0.1 mM to 5 mM, the following potentials were determined (wherein the values for the denatonium benzoate are given in brackets):

SB2AC0: 0.1 mM=−58 mV (−56 mV); 0.5 mM=−56 mV (−45 mV); 1 mM=−54 mV (−36 mV) 5 mM=−37 mV (11 mV).

SB2AN0: 0.1 mM=−73 mV (−71 mV); 0.5 mM=−68 mV (−58 mV); 1 mM=−65 mV (−45 mV); mM=−39 mV (12 mV).

Figure 4:
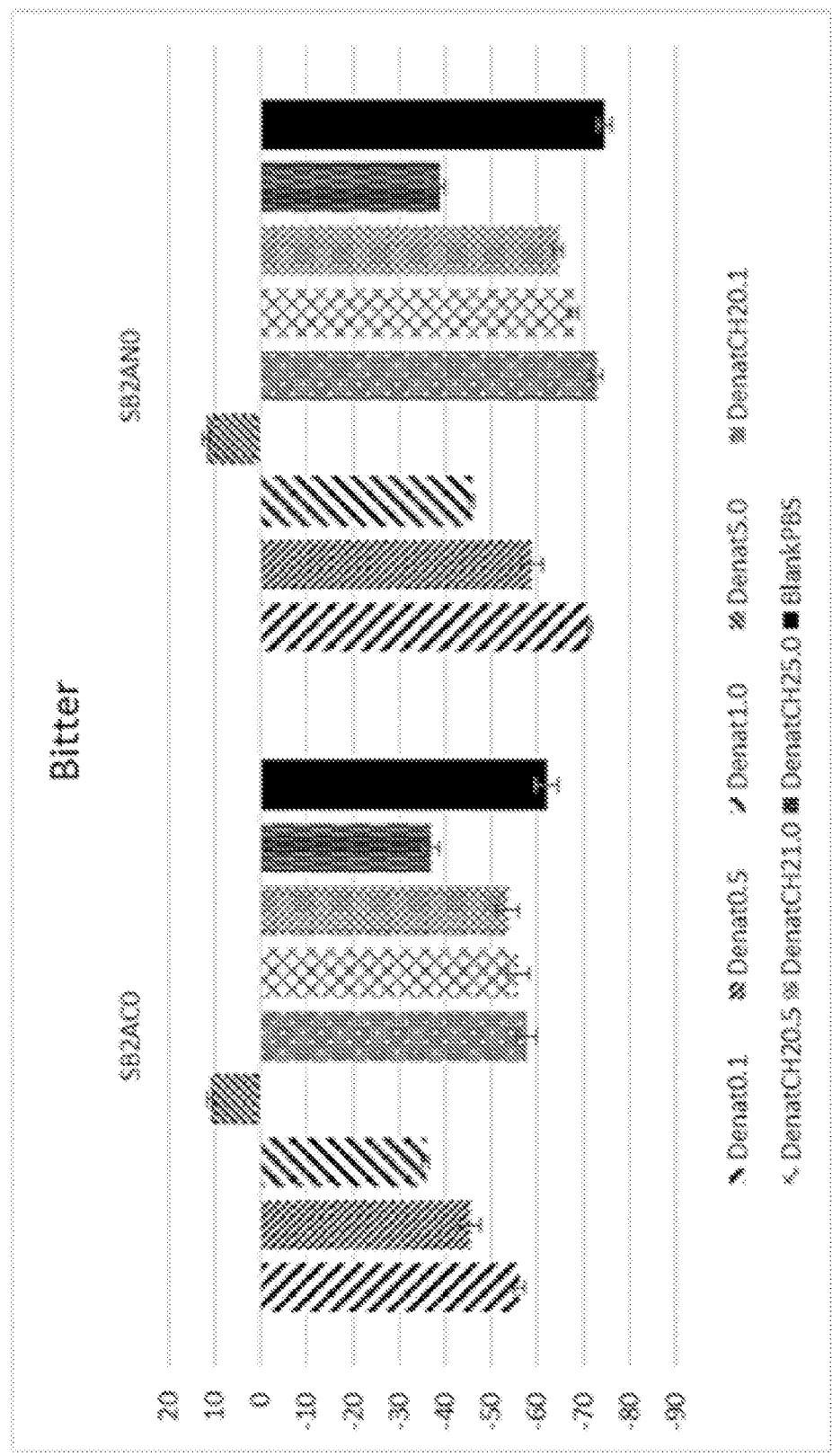
FIG. 4 is a further graphical illustration of potentials measured for compound 2 of the invention ("DenatCH2") and denatonium benzoate ("Denat") at different concentrations, using an electronic tongue, in particular the sensors SB2AC0 and SB2AN0.

A graphical illustration of these results is provided in FIG. 4, wherein compound 2 of the invention is abbreviated as "DenatCH2" and denatonium benzoate abbreviated as "Denat".

This data further illustrates that compounds according to the invention maintain the bitter taste despite the functionalization by the CH2-group, and are perceived similarly to denatonium benzoate as bitter substances.

Example 4: Coupling of Compound 2 with the Peptide QPVV (SEQ ID NO: 1)

The peptide QPVV (SEQ ID NO: 1) used in this example for the coupling with compound 2 of the present invention was synthesized by the inventors using standard techniques. It has the following structure:

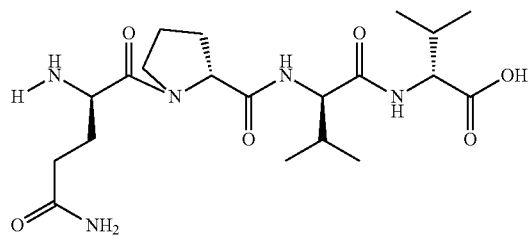 [SMILES: CC(C)[C@@H](NC(=O)[C@H](NC(=O)[C@H]1CCCN1C(=O)[C@H](N)CCC(N)=O)C(C)C)C(=O)O]

Figure 2:
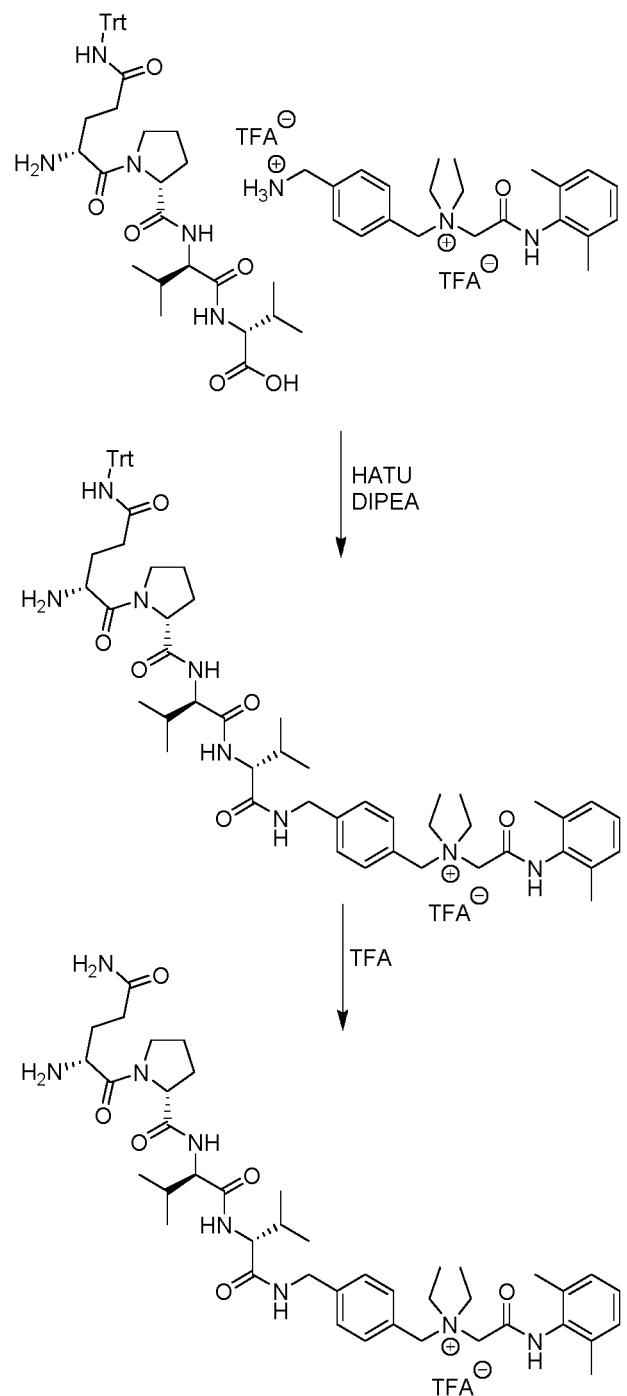
FIG. 2 illustrates the sequence applied in Example 4 for the coupling of triphenylmethyl (Trt)-protected peptide "QPVV" (SEQ ID NO: 2) with compound 2 of the invention and subsequent deprotection of the coupling product.

For the coupling with compound 2 of the present invention, 27 mg of triphenylmethyl (Trt)-protected QPVV (SEQ ID NO: 2) were dissolved in 1 mL dry DMF and then treated with 22.5 mg HATU (0.06 mmol), 20 μL DIPEA (0.1 mmol) and 42 mg of compound 2 (0.07 mmol) obtained in Example 2. This reaction mixture was shaken overnight and afterwards purified by fast protein liquid chromatography (FPLC) (Akta purifier, GE Healthcare) using reversed phase chromatography (RPC) over a C18 column (Phenomenex®) (eluent A: 0.1% TFA in water; eluent B: 0.1% TFA in acetonitrile). The resulting product was subsequently lyophilized. For the deprotection, the lyophilized product was dissolved in trifluoroacetic acid and shaken at room temperature for 1 hour. The obtained product was precipitated in diethylether and purified by chromatography under the same conditions as used before. The sequence applied in this example (including the coupling step and the deprotection step) is illustrated in FIG. 2. As can be taken therefrom, the coupling product was obtained as the TFA salt.

Sum formula: $C_{42}H_{65}N_8O_6^+$ ($C_{42}H_{65}N_8O_6^+C_2F_3O_2^-$)
Molecular mass: 778.01 g/mol (891.03 g/mol)

Example 5: Coupling of Compound 2 with the Peptide DAPV (SEQ ID NO: 3)

The peptide DAPV (SEQ ID NO: 3) used in this example for the coupling with compound 2 of the present invention was synthesized by the inventors using standard techniques. It has the following structure:

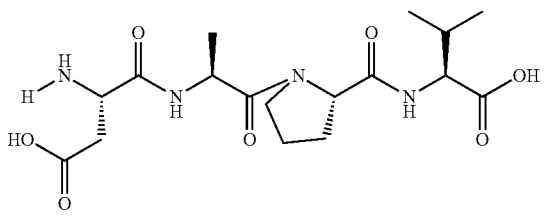 [SMILES: CC(C)[C@H](NC(=O)[C@@H]1CCCN1C(=O)[C@H](C)NC(=O)[C@@H](N)CC(=O)O)C(=O)O]

Figure 3:
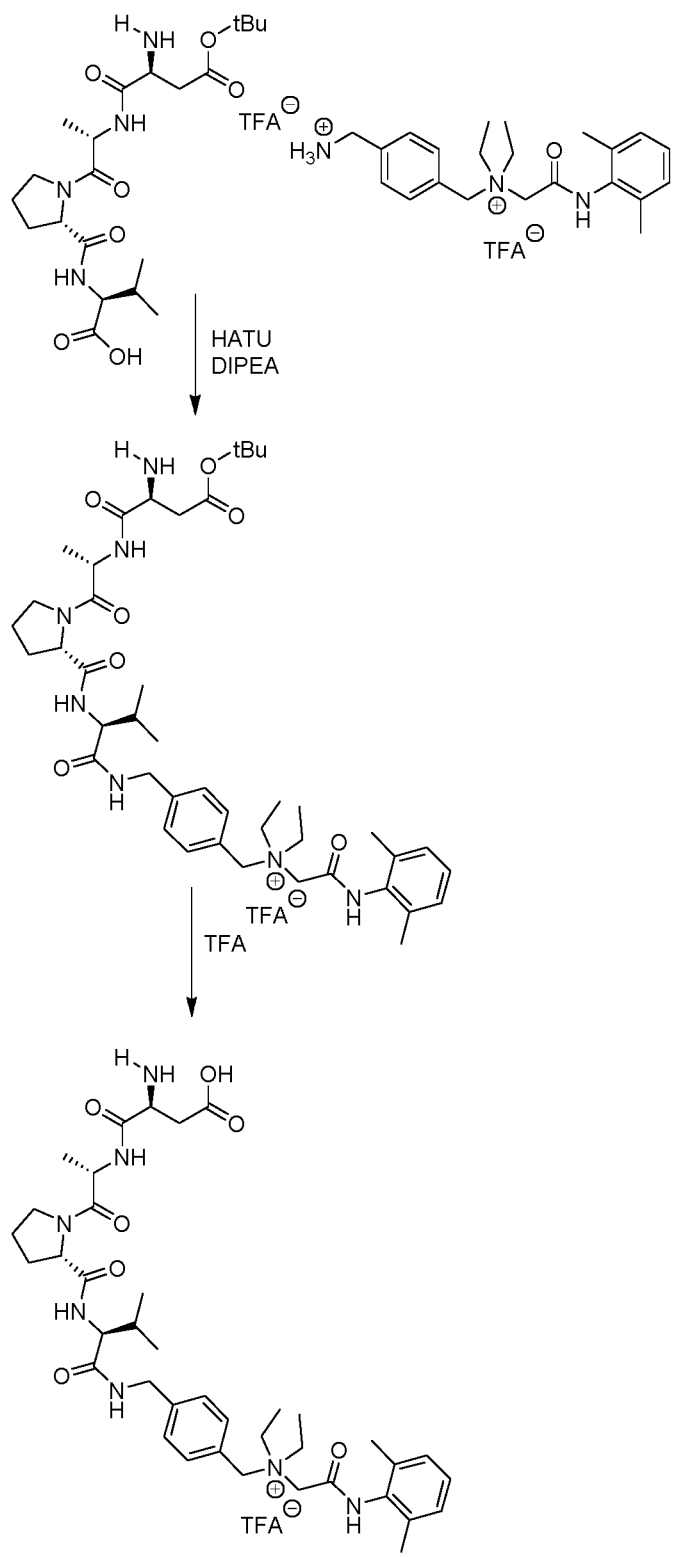
FIG. 3 illustrates the sequence applied in Example 5 for the coupling of tert-butyl (tBu)-protected peptide "DAPV" (SEQ ID NO: 4) with compound 2 of the invention and subsequent deprotection of the coupling product.

For the coupling with compound 2 of the present invention, 31 mg of tert-butyl (tBu)-protected DAPV (SEQ ID NO: 4) were solved in 1 mL dry DMF and then treated with 38 mg HATU (0.1 mmol), 35 μL DIPEA (0.2 mmol) and 72 mg of compound 2 (0.1 mmol) obtained in Example 2. This reaction mixture was shaken overnight. Purification was carried out analogously to Example 4. The sequence applied in this example (including the coupling step and the deprotection step) is illustrated in FIG. 3. As can be taken therefrom, the coupling product was obtained as the TFA salt.

Sum formula: $C_{39}H_{58}N_7O_7^+$ ($C_{39}H_{58}N_7O_7^+C_2F_3O_2^-$)
Molecular mass: 736.9 g/mol (849.95 g/mol)

Example 6: Taste Testing of Compound 2 Coupled with the Peptide GPQGIAGA (SEQ ID NO: 5)

Compound 2 of the present invention was coupled with the peptide "GPQGIAGA" (SEQ ID NO: 5), which has the following structure:

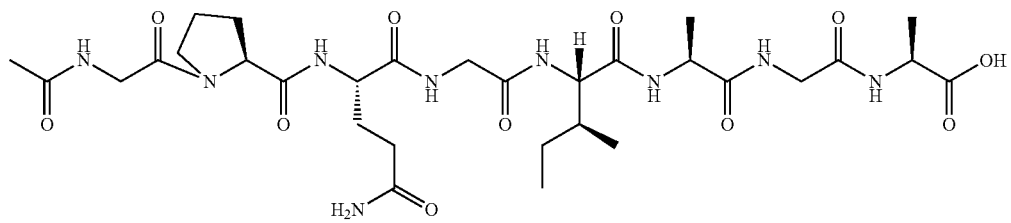 [SMILES: CC[C@H](C)[C@H](NC(=O)CNC(=O)[C@H](CCC(N)=O)NC(=O)[C@@H]1CCCN1C(=O)CNC(C)=O)C(=O)N[C@@H](C)C(=O)NCC(=O)N[C@@H](C)C(=O)O]

For the coupling, 1 equivalent of the triphenylmethyl (Trt)-protected peptide GPQGIAGA (SEQ ID NO: 6) were dissolved in dry DMF and then treated with 3 equivalents of HATU, 6 equivalents of DIPEA and 1.9 equivalents of compound 2. This reaction mixture was shaken for two days and afterwards purified by chromatography (Akta purifier (GE Healthcare), reversed-phase chromatography (RPC), Eluent A: 0.1% TFA in water, Eluent B: 0.1% TFA in acetonitrile).

For the deprotection, the lyophilized product was dissolved in trifluoroacetic acid and shaken at room temperature for 1 hour. The obtained product was precipitated in diethylether and purified by chromatography (Akta purifier (GE Healthcare), reversed-phase chromatography (RPC), Eluent A: 0.1% TFA in water, Eluent B: 0.1% TFA in acetonitrile)

Figure 5:
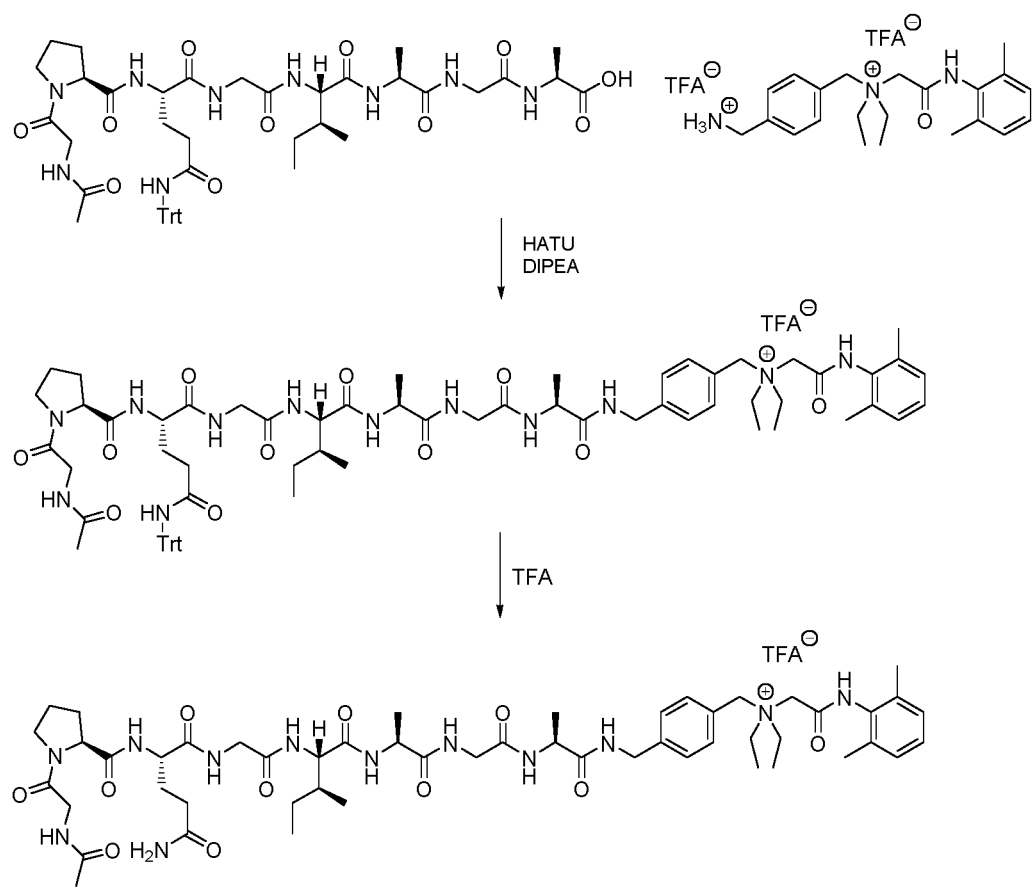
FIG. 5 illustrates the reaction sequence applied in Example 6 for the synthesis of a coupling product of compound 2 according to this invention and the peptide "GPQGIAGA" (SEQ ID NO: 5).

This reaction sequence is graphically illustrated in FIG. 5, which also shows the resulting product of this coupling (in the following referred to as the coupling product or "SL10K").

The potential of the coupling product was determined in comparison with denatonium benzoate using an electronic tongue, in particular the sensors SB2AC0 and SB2AN0. The following potentials were determined (wherein the values for the denatonium benzoate are given in brackets):

SB2AC0: 0.1 mM=−113 mV (−107 mV); 0.5 mM=−114 mV (−89 mV); 1.0 mM=−124 mV (−73 mV)

SB2AN0: 0.1 mM=−127 mV (−120 mV); 0.5 mM=−134 mV (−94 mV); 1.0 mM=−156 mV (−75 mV)

Figure 6:
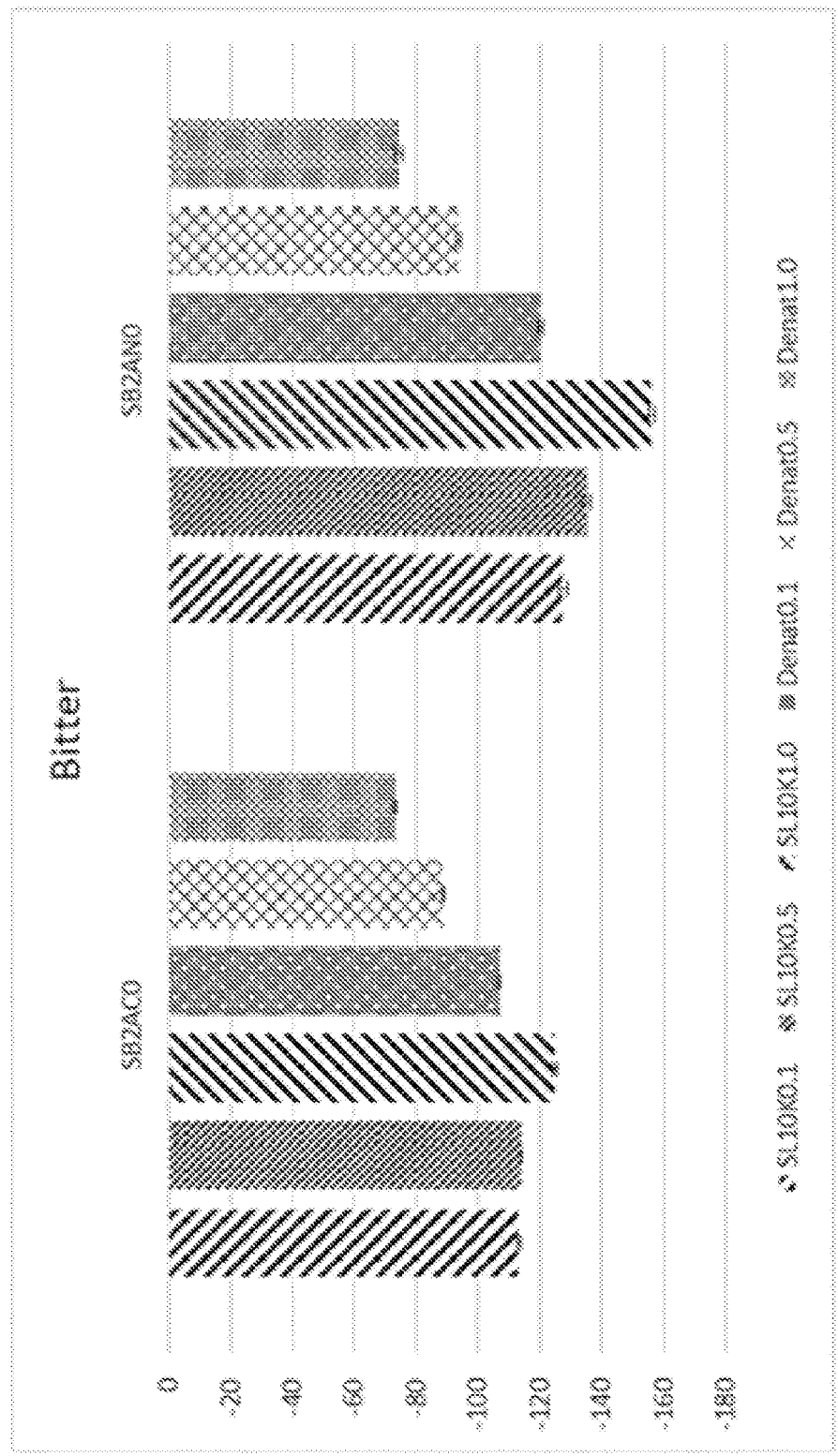
FIG. 6 is a graphical illustration of potentials measured for the coupling product ("SL10K") prepared in Example 6 and denatonium benzoate ("Denat") at different concentrations, using an electronic tongue, in particular the sensors SB2AC0 and SB2AN0.

A graphic illustration of these results is provided in FIG. 6, wherein the coupling product is abbreviated as "SL10K" and denatonium benzoate as "Denat".

The data according to FIG. 6 shows that for denatonium benzoate, the mV values increase with higher concentration of the compound. This indicates that the perception of the bitter taste of the compound increases at higher concentration.

In contrast thereto, for the coupling product, the mV values decrease with higher concentration. This indicates that the denatonium derivative according to compound 2 is not perceived as a bitter compound when coupled to the peptide. The bitter taste is only perceivable when the coupling product is cleaved and the denatonium derivative according to compound 2 is released (as has been shown in Example 3 above). This is particularly useful for diagnostic purposes.

The invention claimed is:

1. A compound of general formula (I)

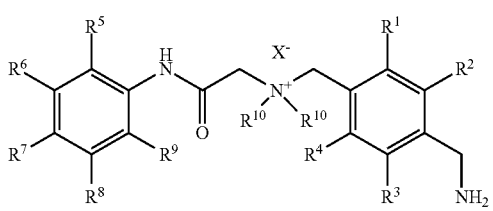

or a salt thereof, wherein:

$X^-$ is selected from the group consisting of a halide, pseudohalide, sulphate, benzoate, acetate, trifluoroacetate, hydroxide, saccharinate and capsaicinate;

$R^{10}$ is hydrogen or a C1-C10-alkyl; and $R^1$-$R^9$ independently are selected from the group consisting of hydrogen, halogen, C1-C5-alkyl, C1-C4-alkoxy, and C1-C20-alkoxycarbonyl.

2. The compound according to claim 1, wherein:

$X^-$ is selected from the group consisting of a halide, pseudohalide, sulphate, benzoate, acetate and trifluoroacetate;

$R^{10}$ is a C1-C4-alkyl;

$R^1$-$R^4$ are each hydrogen;

$R^5$ is a C1-C4-alkyl;

$R^9$ is a C1-C4-alkyl; and $R^6$-$R^8$ are each hydrogen.

3. The compound according to claim 1, wherein:

$X^-$ is trifluoroacetate;

$R^{10}$ is ethyl;

$R^5$ is methyl;

$R^9$ is methyl;

$R^1$-$R^4$ are each hydrogen; and $R^6$-$R^8$ are each hydrogen.

4. The compound according to claim 1, wherein said compound is formulated for use as a bitter substance in medicine, pharmaceutics and/or diagnostics.

5. A method for preparing a compound of general formula (I)

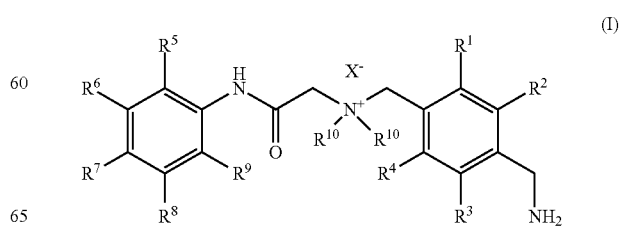

or a salt thereof, said method comprising the following steps:

a) reacting a compound of general formula (II):

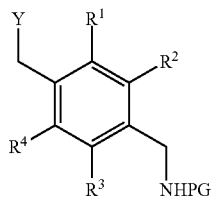

(II)

with a compound of general formula (III):

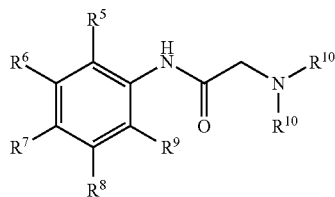

(III)

resulting in a compound of general formula (IV):

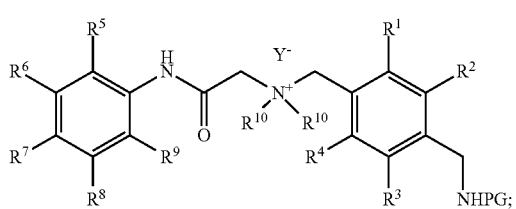

(IV)

and b) deprotecting the compound of general formula (IV) to form the compound of general formula (I) or a salt thereof, wherein, in the compounds of general formulae (I), (II), (III) and (IV):

$R^1$-$R^{10}$ and $X^-$ are as defined in claim 1;

Y is a halogen or pseudohalogen;

$Y^-$ is a halide or pseudohalide corresponding to Y; and

PG is an amino protection group selected from the group consisting of tert-butyloxycarbonyl (Voc), benzyloxycarbonyl (Cbz), fluorenylmethoxycarbonyl (Fmoc) and allyloxycarbonyl (alloc).

6. The method according to claim 5, wherein step a) is performed in a solvent-free melt.

7. The method according to claim 6, wherein a mixture of the compound of general formula (II) and the compound of general formula (III) is heated for 1 to 30 minutes at temperatures in the range of 60 to 120° C.

8. The method according to claim 5, wherein 1 molar equivalent of the compound of general formula (II) is reacted with 1.4 to 1.8 molar equivalents of the compound of general formula (III).

9. The method according to claim 5, wherein, in the compound of general formula (II), Y is Br and, in the compound of general formula (IV), $Y^-$ is $Br^-$.

10. The method according to claim 5, wherein PG in the compound of general formulae (II) and (IV) is tert-butyloxycarbonyl (Boc).

11. The method according to claim 10, wherein the step of deprotecting the compound of general formula (IV) set forth in step b) is performed solvent-free using trifluoroacetic acid.

12. The method according to claim 5, wherein:

$X^-$ is selected from the group consisting of a halide, pseudohalide, sulphate, benzoate, acetate and trifluoroacetate;

$R^{10}$ is a C1-C4-alkyl;

$R^1$-$R^4$ are each hydrogen;

$R^5$ is a C1-C4-alkyl;

$R^9$ is a C1-C4-alkyl; and $R^6$-$R^8$ are each hydrogen.

13. The method according to claim 5, wherein:

$X^-$ is trifluoroacetate;

$R^{10}$ is ethyl;

$R^5$ is methyl;

$R^9$ is methyl;

$R^1$-$R^4$ are each hydrogen; and $R^6$-$R^8$ are each hydrogen.

14. A coupling product for use in medicine, pharmaceutics and/or diagnostics, said coupling product comprising the compound according to general formula (I) as defined in claim 1 and a peptide or a protein, wherein the compound of general formula (I) and the peptide or the protein are connected via a peptide bond between the aminomethyl-group of the compound of general formula (I) and a carboxyl-group (COOH-group) of the peptide or protein.

15. A method for producing a coupling product comprising the compound according to general formula (I) or a salt thereof as defined in claim 1 and a peptide or protein, said method comprising the step of coupling the compound of general formula (I) or a salt thereof with the peptide or protein by forming a peptide bond between the aminomethyl-group of the compound of general formula (I) or the salt thereof and a carboxyl-group of the protein or peptide.

16. The method according to claim 15, wherein the peptide or protein used in the coupling with the compound of general formula (I) or the salt thereof is protected by a protection group, and the protection group is cleaved after the coupling.

17. The method according to claim 15, wherein the compound of general formula (I) or the salt thereof and the peptide or protein is coupled in the presence of a coupling agent and a base.

18. The method according to claim 17, wherein the coupling agent is O-(7-azabenzotriazol-1-yl)-N,N,N',N'-tetramethyluronium-hexafluorphosphate (HATU) and the base is diisopropylethylamine (DIPEA).

* * * * *